United States Patent
Aono

(10) Patent No.: US 8,261,802 B2
(45) Date of Patent: Sep. 11, 2012

(54) DEVICE FOR MOUNTING ELASTIC MEMBER IN ABSORPTIVE ARTICLE

(75) Inventor: Syumei Aono, Sekura (JP)

(73) Assignee: Daio Paper Corporation, Ehime (JP)

( * ) Notice: Subject to any disclaimer, the term of this patent is extended or adjusted under 35 U.S.C. 154(b) by 731 days.

(21) Appl. No.: 11/887,300

(22) PCT Filed: Mar. 28, 2006

(86) PCT No.: PCT/JP2006/306364
§ 371 (c)(1),
(2), (4) Date: Jul. 14, 2008

(87) PCT Pub. No.: WO2006/106696
PCT Pub. Date: Oct. 12, 2006

(65) Prior Publication Data
US 2010/0230056 A1   Sep. 16, 2010

(30) Foreign Application Priority Data
Mar. 31, 2005   (JP) ................................ 2005-103884

(51) Int. Cl.
*B32B 37/00* (2006.01)
*B29B 65/00* (2006.01)

(52) U.S. Cl. ........ 156/538; 156/436; 156/494; 156/552; 242/615.3

(58) Field of Classification Search ................. 156/436, 156/494, 552, 538; 242/615.3
See application file for complete search history.

(56) References Cited

U.S. PATENT DOCUMENTS

| 373,151 A | * | 11/1887 | Northup | .......................... 139/86 |
| 6,808,582 B2 | * | 10/2004 | Popp et al. | .................... 156/229 |

FOREIGN PATENT DOCUMENTS

| JP | 59-069358 | 4/1984 |
| JP | 04-028363 | 1/1992 |
| JP | 07-265357 | 10/1995 |
| JP | 07-299094 | 11/1995 |
| JP | 10-211230 | 8/1998 |
| JP | 11-036103 | 2/1999 |
| JP | 11-332913 | 12/1999 |
| JP | 2001-181943 | 7/2001 |
| JP | 2001-204762 | 7/2001 |
| JP | 2001-258931 | 9/2001 |
| JP | 2003-38565 | 2/2003 |
| JP | 2004-159866 | 6/2004 |

* cited by examiner

*Primary Examiner* — Linda L Gray
(74) *Attorney, Agent, or Firm* — DLA Piper LLP (US)

(57) ABSTRACT

A device for installing an elastic member including a conveying line for continuously conveying sheets to be mounted, a feeding device for continuously feeding elastic members, and a guide for guiding the elastic members fed from the feeding device, to installation positions on the raw materials to be mounted on the conveying line. The guide has an upper section and a lower section detachably attached to the upper section. A guide path whose surrounding is closed is formed between the upper section and the lower section. The elastic members are guided to the installation positions through the guide path.

6 Claims, 20 Drawing Sheets

(A) DEVELOPED STATE (B) PRODUCT STATE (A)

(B)

(A)

(B)

DEVICE FOR MOUNTING ELASTIC MEMBER IN ABSORPTIVE ARTICLE

TECHNICAL FIELD

The present invention relates to equipment for mounting elastic members such as rubber threads in a predetermined position of raw materials to be mounted, such as sheet, by a guide in production of absorptive articles, such as disposable paper diapers and sanitary napkins, etc.

BACKGROUND ART

For example, absorbents for absorption of a body fluid is worn by a human body in wearing of pants-type disposable paper diapers. For this reason, conventionally, elastic members are arranged in various directions and in various positions in sheets for holding of the absorbent, etc. to improve fitting property on the human body.

For example, as shown in FIG. 16, there is disclosed a pants-type disposable diaper that includes a liquid-permeable top sheet 50, a liquid-impermeable back sheet 51, and an absorbent 52 arranged between those sheets 50 and 51. The disposable diaper is made to fit the human body in such a manner that waist portion elastic members 48, 48, . . . are arranged along the waist opening, leg portion elastic members 53, 53, . . . are arranged in the two leg openings substantially continuously along the peripheral edges, and hip portion elastic members 49, 49, . . . are arranged around the hip surrounding (Refer to Patent Document 1).

In a case where the elastic stretchable members are arranged individually and independently at the three portions of the waist opening, the leg openings and the hip surrounding, as in the aforementioned disposable diaper, the minimum fit necessary for the paper diaper can be obtained but the satisfaction of the user is not always obtained.

As shown in FIG. 17, there is disclosed a disposable diaper, which includes a lower curved gather 54 of the trunk gathers as the gather for the abdomen side and/or the back side in order to prevent the slip-down of the diaper. The lower curved gather 54 is formed and curved at least to the crotch portion, and has a lowermost portion thereof positioned lower than the uppermost end of the leg openings. (refer to Patent Document 2).

Furthermore, as shown in FIG. 18, there is disclosed a pants-type disposable diaper comprising an absorbent body and an armoring member, wherein first stretchable elastic members 55, 55, . . . , and second stretchable elastic members 56, 56, . . . , each composed of a plurality of stretchable elastic materials are located on the front and the back of the armoring member. These stretchable elastic members 55, . . . , and 56, . . . , individually extend from one side edge portion of one of the front and the back through the crotch portion to the other side edge portion, such that at least their portions are arranged along the paired leg surrounding openings and at a predetermined spacing at the crotch portion.

Furthermore, as shown in FIG. 19, in order to further prevent the slip-down, there is disclosed a disposable pants-type diaper. The diaper has a body including a top sheet, a back sheet and an absorbent, and the body comprises an abdomen side portion and a back side portion. The two right and left side edge portions of the abdomen side portion and the back side portion are jointed and fixed to form a waist opening and leg openings. In the waist opening and the leg openings arranged are a waist elastic member 57 and leg elastic members 58 to form gathers substantially continuing along their whole peripheral edge portions. A plurality of hip surrounding elastic members 59, 59, . . . are arranged on the abdomen side and/or the back side of the hip surrounding elastic members. The hip surrounding elastic members 59, 59, . . . are arranged in such a displacement to the side of the crotch portion that the displacements of the hip surrounding elastic members 59, 59, . . . , have a largest value at the central portion of the abdomen side portion (refer to Patent Document 4).

Moreover, as shown in FIG. 20, there is disclosed a pants-type paper diaper having elastic ridges 60, 60, . . . , extending in a transverse direction arranged in a gather constitution having no intersection all over the front and the back of the pants. The elastic ridges 60, 60, . . . , of the front and the back are substantially arranged with uniform spacing in a longitudinal direction on the right and left seal lines, and are more bulged and curved toward the crotch portion as they come closer to the intermediate portion (refer to Patent Document 5).

On the other hand, in production of such a pants-type paper diaper, it is general that in a case of mounting an elastic member in a direction along the trunk surrounding, or the hip surrounding, for example, the elastic member is continuously supplied with respect to a conveying line for continuous conveying raw materials to be mounted, and simultaneously the elastic member is guided and mounted through a guide located on the conveying line to a mounting position on the raw materials to be mounted (for example, refer to Patent Document 6 and Patent Document 7).

Guides having a hook shape have conventionally been used as the guide in this case. However, due to possibility of catch missing of an elastic member from the hook, and due to impossibility of parallel mounting with a predetermined spacing of a plurality of elastic members, in recent years, devices having passages with guides having a closed circumference for guiding the elastic member have been developed for use.

However, necessity for passing a new elastic member for the passage at the time of cut or replacement etc. of the elastic members forces insertion of the elastic member having poor slipping property from one side through the narrow passage, resulting in significantly complicated operations.

Patent Document 1: JP-A-07-265357
Patent Document 2: JP-A-07-299094
Patent Document 3: JP-A-11-36103
Patent Document 4: JP-A-2001-258931
Patent Document 5: JP-A-2001-204762
Patent Document 6: JP-A-04-28363
Patent Document 7: JP-A-11-332913

SUMMARY OF THE INVENTION

Therefore, an object of the present invention is to achieve simplification of works to allow an elastic member to pass through a guide path.

Hereinafter, the present invention will be described.

The present invention provides a device for mounting an elastic member in an absorptive article, comprising:
a conveying line for continuously conveying a raw material to be mounted;
a feeding device for continuously feeding the elastic member; and
a guide for guiding the elastic member fed from the feeding device to a mounting position on the raw material to be mounted on the conveying line,
wherein
the guide has a first part and a second part detachably attached to the first part, a guide path having a closed circumference is formed between the first part and the second part so that the elastic member can be guided to the mounting position through the guide path; and a joint of the first part and the second part exposed to an interior surface of the guide path is not located in both sides of the interior surface of the guide path in the cross direction.

In the device for mounting an elastic member in an absorptive article according to the present invention, a groove passing through from one peripheral edge to another peripheral edge is formed, in a face of the first part opposed to the second part and in a face of the second part opposed to the first part, and these grooves are coupled together to form the guide path.

In the device for mounting an elastic member in an absorptive article according to the present invention, the guide is configured to have a plurality of the guide paths to be juxtaposed in a cross direction.

In the device for mounting an elastic member according to the present invention, the guide path is a circular hole extending along a machine direction, and a joint of the first part and the second part exposed to an interior surface of the guide path is not located within angle ranges of ±45 degrees with respect to the cross direction of angle ranges around a center of the guide path.

In the present invention, the guide path is formed between the first part and the second part, and simultaneously the second part is configured to be detachable from the first part. It is simple and preferable that the guide path is configured to be formed by unification of a groove in the face of the first part opposed to the second part and a groove in the face of the second part opposed the first part.

Such a configuration allows an opened state of a portion of the peripheral surface of the guide path over the whole passage by removal of the second part. Accordingly, in case of insertion of the elastic member to the guide path, removal of the second part allows insertion of the elastic member into the guide path from an open part on the side, resulting in significantly easier operation as compared with conventional operation of inserting the elastic member from one side of the guide path. Needless to mention, the present invention does not necessarily need operations by removal of the second part.

The present invention can be advantageously applied when a plurality of guide paths are disposed in parallel, which is not necessarily required in the present invention, since the inserting operation of the elastic member tends to be especially complicated.

In the case of guiding the elastic member in a curved state by oscillation of the guide, when the joint of the first part and the second part exposed in the interior surface of the guide pass is located in both sides in a CD direction of the interior surface of the guide path, due to such oscillation, friction may be caused between the joint and the elastic member, thereby, yarn breakage of the elastic member may be caused. Accordingly, in the present invention the joint is configured so as not to be located in the both sides in a cross direction.

BRIEF DESCRIPTION OF THE DRAWINGS

FIG. 7(A) is a schematic diagram, and FIG. 7(B) is a principal part plan view;

FIG. 16(A) is a developed view, and FIG. 16(B) is a product state view:

FIG. 20(A) is a front view, and FIG. 20(B) is a developed view.

BEST MODE FOR CARRYING OUT THE INVENTION

Hereinafter, based on an example of application in a pants-type disposable paper diaper, detailed description will be given about one embodiment of the present invention. It can easily be understood that the present invention is applicable for tape type disposable paper diapers attached with tapes in both side parts, absorptive articles of other kinds, such as various sanitary napkins, etc.

Figure 1:
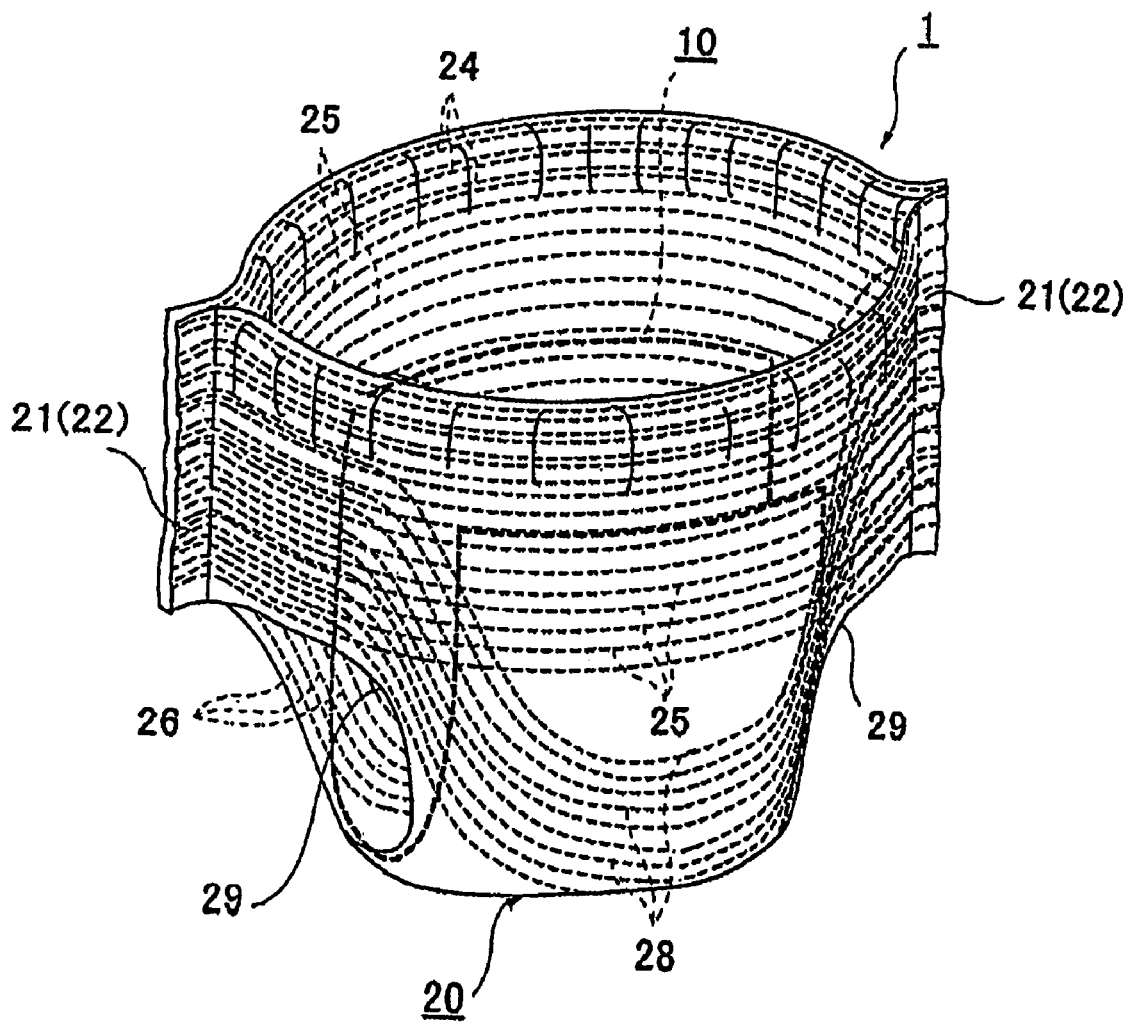
FIG. 1 is an external view of a product state of a pants-type disposable paper diaper 1.
Figure 2:
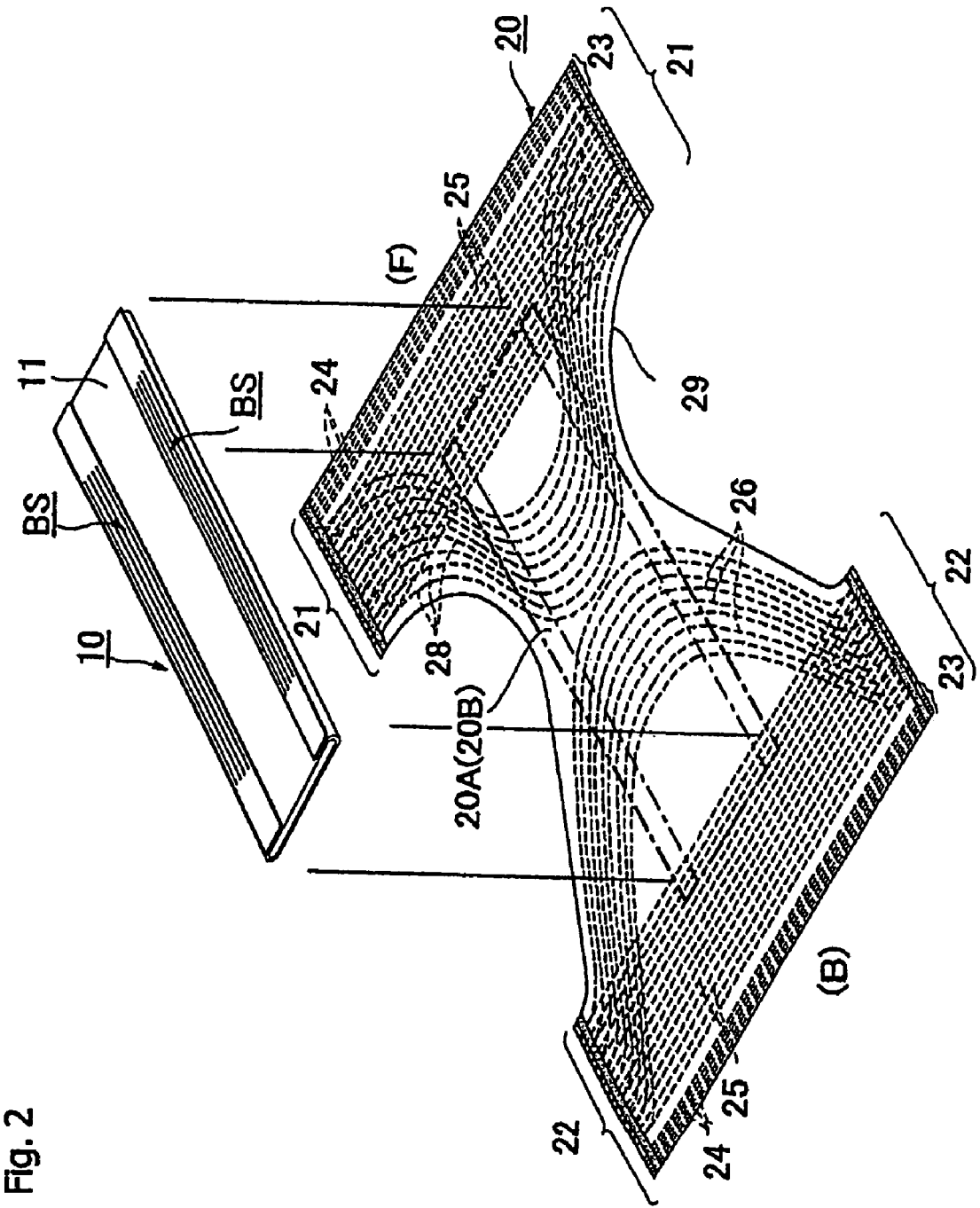
FIG. 2 is an assembly view in a developed state.

FIG. 1 is an external view of a product state of a pants-type disposable paper diaper 1 according to an embodiment. FIG. 2 is an assembly diagram in a developed state. The pants-type disposable paper diaper 1 (hereinafter referred to only as paper diaper) comprises an absorbent body 10 having an interposing absorbent 13, such as fluffy pulp between a liquid-permeable surface sheet 11 comprising nonwoven fabric etc., and a liquid tight sheet 12 comprising polyethylenes etc., and an armoring sheet 20 integrally formed in an outside surface side of the absorbent body 10. In production thereof, the absorbent body 10 is adhered with adhesives, such as hot melt adhesives, and integrated on an upper surface side of the armoring sheet 20, subsequently the absorbent body 10 and the armoring sheet 20 are folded in a longitudinal direction, the both side parts are mutually joined by hot welding or with hot melt adhesives, thereby to obtain a pants-type paper diaper having an waist opening and a pair of right and left leg openings formed thereto.

Hereinafter, descriptions will be given in an order of the absorbent body 10 and the armoring sheet 20.

(Structure of Absorbent Body)

Figure 5:
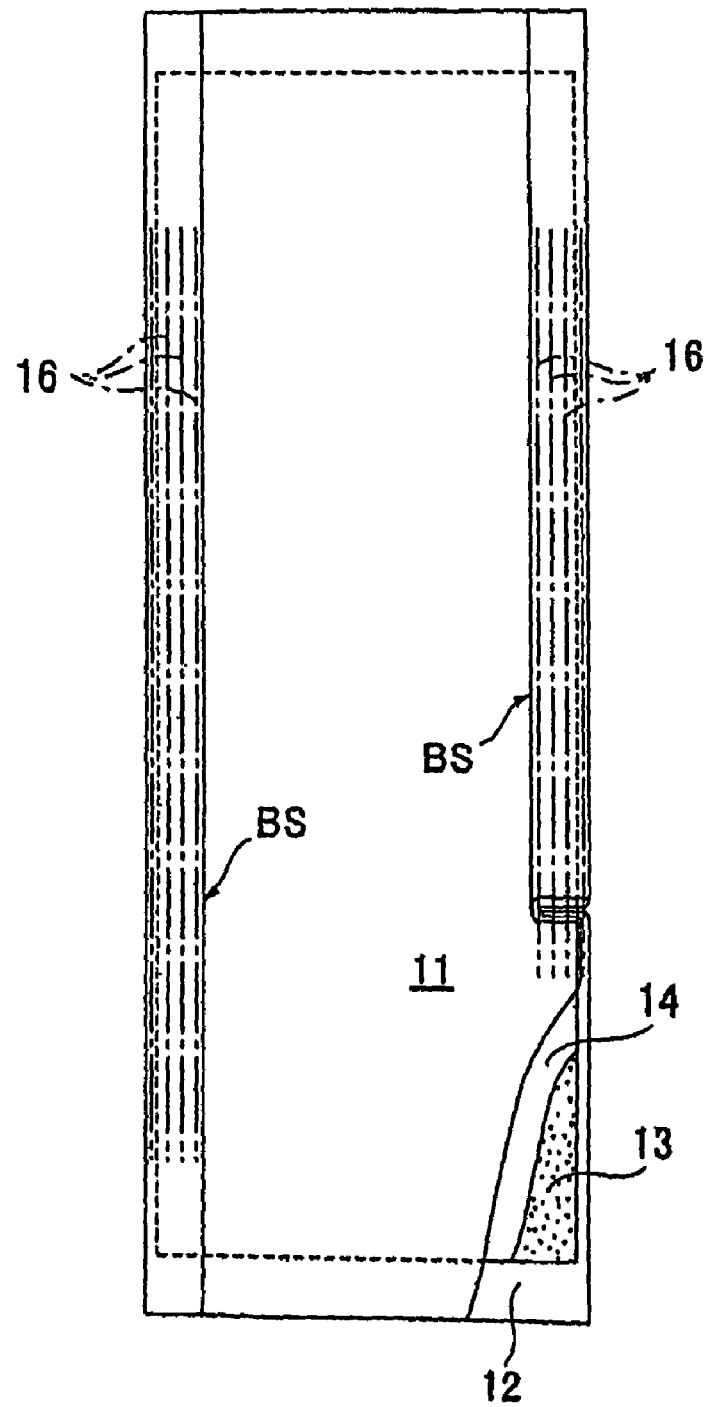
FIG. 5 is a top plan view of an absorbent body 10.
Figure 6:
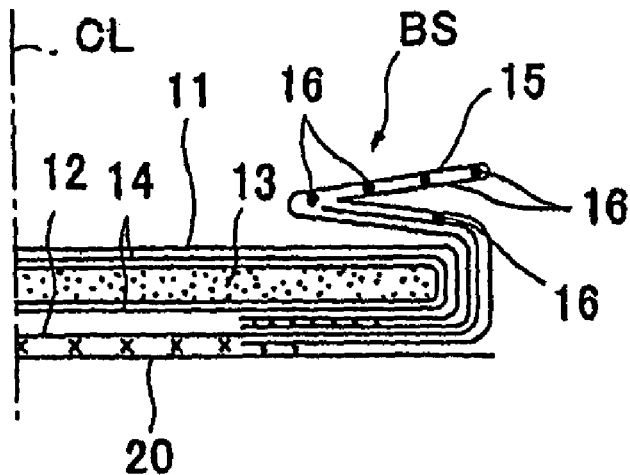
FIG. 6(A) is a transverse section of one half of the absorbent body 10 in a developed state, and 6(B) is a view showing the product state.
Figure 6:
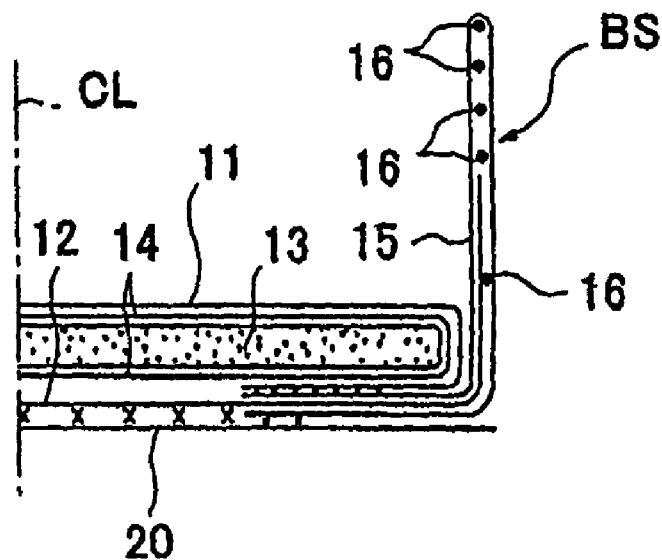

As shown in FIG. 5 and FIG. 6, the absorbent body 10 has a structure having the absorbent 13 such as fluffy pulp interposed between the liquid-permeable surface sheet 11 comprising nonwoven fabrics etc., and the liquid tight sheet 12 comprising polyethylenes etc., and has a function for absorbing and holding a body fluid.

As the liquid-permeable surface sheet 11 for covering the surface side (contact surface side to the human skin) of the absorbent 13, nonwoven fabrics with or without pores therein, porous plastic sheets, etc. are suitably used. Examples of raw material fibers that form the nonwoven fabric include synthetic fibers, such as olefins as made of polyethylenes or polypropylenes, polyesters, and polyamides; and furthermore regenerated fibers, such as rayon and cuprammonium rayon; and natural fibers, such as cotton. Nonwoven fabrics obtained by proper processing methods, such as spun lace methods, spun bond methods, thermal bond methods, melt blown method, and needle punch methods may be used. Of these processing methods, the spun lace method can exhibit excellent flexibility and drape property, and the thermal bond method can exhibit excellent softness and bulkiness. When the liquid-permeable surface sheet 11 has a large number of formed through-holes, it allows quick absorption of urine etc., resulting in excellent dry touch. The liquid-permeable surface sheet 11 encloses the side edge portion of the absorbent 13, and extends to the back side the absorbent 13.

Although liquid-impermeable plastic sheets, such as made of polyethylenes or polypropylenes, are used as the liquid tight sheet 12 for covering the back side (non-contact surface side to the human skin) of the absorbent 13, in recent years, sheets having moisture permeability are suitably used in view of prevention of stuffiness. The water-tight/moisture permeable sheets are microporous sheets obtained by uniaxial or biaxial drawing of, for example, a sheet formed by melt-kneading inorganic fillers in olefin resins, such as polyethylenes and polypropylenes. Since the sheets have rigidity lower than that of nonporous sheets if they have the same thickness, the sheets can exhibit superior flexibility.

Materials obtained by molding a fluffy pulp and water absorptive polymer are suitably used as the absorbent 13. For example, the water absorptive polymer may be mixed as a granular powder into the pulp forming the absorbent. Examples of the pulp include materials including chemical pulp obtained from wood; cellulose fibers, such as dissolving pulp; and artificial cellulose fibers, such as rayons and acetates. The long softwood pulp having larger fiber length than that of the hardwood pulp may be preferably used with respect of function and price. Of course, publicly known absorbents other than them are also employable. Furthermore, the absorbent 13 may be wrapped by the liquid-permeable sheet 14, such as crepe paper, if needed, for improvement in shape retaining, and in diffusibility of body fluid that has transmitted through the liquid-permeable surface sheet 11. As is illustrated in the figure, the absorbent 13 may have a shape having a width with a narrower crotch portion than the width of the back side portion and abdomen side portion, or may have a rectangle shape.

Three-dimensional gathers BS fitting the leg surroundings are preferably formed in both side parts of the absorbent body 10. The three-dimensional gather BS is formed with a gather nonwoven fabric 15. As the gather nonwoven fabric suitably used is a nonwoven fabric folded into a double liner sheet as shown in FIG. 6. The gather nonwoven fabric encloses the side edge portion of the absorbent 13 enclosed with the liquid-permeable surface sheet 11 from the upside, extending to the back side of the absorbent 13 to be adhered. In more detail, in the intermediate part in the longitudinal direction of the paper diaper, the gather nonwoven fabric 15 is made to adhere in a section from the intermediate portion in a width direction to the back side of the absorbent 13 with a hot melt adhesive etc., leaving a port ion having three-dimensional gathers BS formed therein. In a front edge in and in a rear edge in a longitudinal direction, a section from the intermediate portion in a width direction to one of the edges is made to adhere in a section covering the back side of the absorbent 13, and simultaneously the gather nonwoven fabric 15 is made to adhere with a hot melt adhesive etc., while folding up a portion in which three-dimensional gathers BS is to be formed in an upper face portion of the absorbent 13.

A plurality of elastic fiber stretchable members 16, 16, . . . are arranged in the gather nonwoven fabric 15 formed with a double liner sheet nonwoven fabric in a raised end side portion. In order to form the three-dimensional gather BS, the elastic fiber stretchable members 16, 16, . . . , force the nonwoven fabric part projecting from the side line part of the absorbent to raise with an elastic stretching force, as shown in a product state in FIG. 6(B).

The liquid tight sheet 12 enters inside of the double liner sheet-shaped gather nonwoven fabric 15, and a leakage preventing wall is formed in the lower end side of the three-dimensional gather BS as shown in FIG. 6. An opaque sheet is desirably used as the liquid tight sheet 12 so that brown colors, such as defecation and urine, may not be exposed on the surface. Preferable examples of opacificated films include plastics films containing pigments and fillers therein, such as calcium carbonate, titanium oxides, zinc oxide, white carbon, clay, talc, and barium sulfate.

Available examples of the elastic fiber stretchable members 16 include usual raw materials, such as styrene based rubbers, olefin rubbers, urethane rubbers, ester rubbers, polyurethanes, polyethylenes, polystyrenes, styrene butadienes, silicones, and polyesters. In order to realize invisibility from outside, the elastic fiber stretchable member 16 preferably has a thickness of 925 dtex or less, and is arranged under conditions of a tension of 150 to 350%, and a spacing of 7.0 mm or less. Tape shaped elastic stretchable members having a certain amount of width may be used as substitution of the elastic fiber stretchable member.

As in a case of the liquid-permeable surface sheet 11, examples of raw material fibers for forming the above-mentioned gather nonwoven fabric 15 may include synthetic fibers, such as olefin fibers as of polyethylenes or polypropylenes, polyester fibers, and amido fibers, etc. regenerated fibers, such as rayons and cuprammonium rayons, and natural fibers, such as cotton. Nonwoven fabrics obtained by proper processing methods, such as a spunbond method, a thermal bonding method, a melt blown method, and a needle punch method, may be used, and in order to especially avoid stuffiness, nonwoven fabrics having suppressed basis weight and excellent gas permeability are advantageously used. Furthermore, in order to avoid penetration of urine and diaper rash and to increase feeling (dry feeling) to the human skin, as the gather nonwoven fabric 15 desirably used are nonwoven fabrics coated with silicon based, paraffin metal based, and alkyl chromic chloride based water repellents to apply a water-repellent finish.

(Structure of Armoring Sheet 20)

Figure 3:
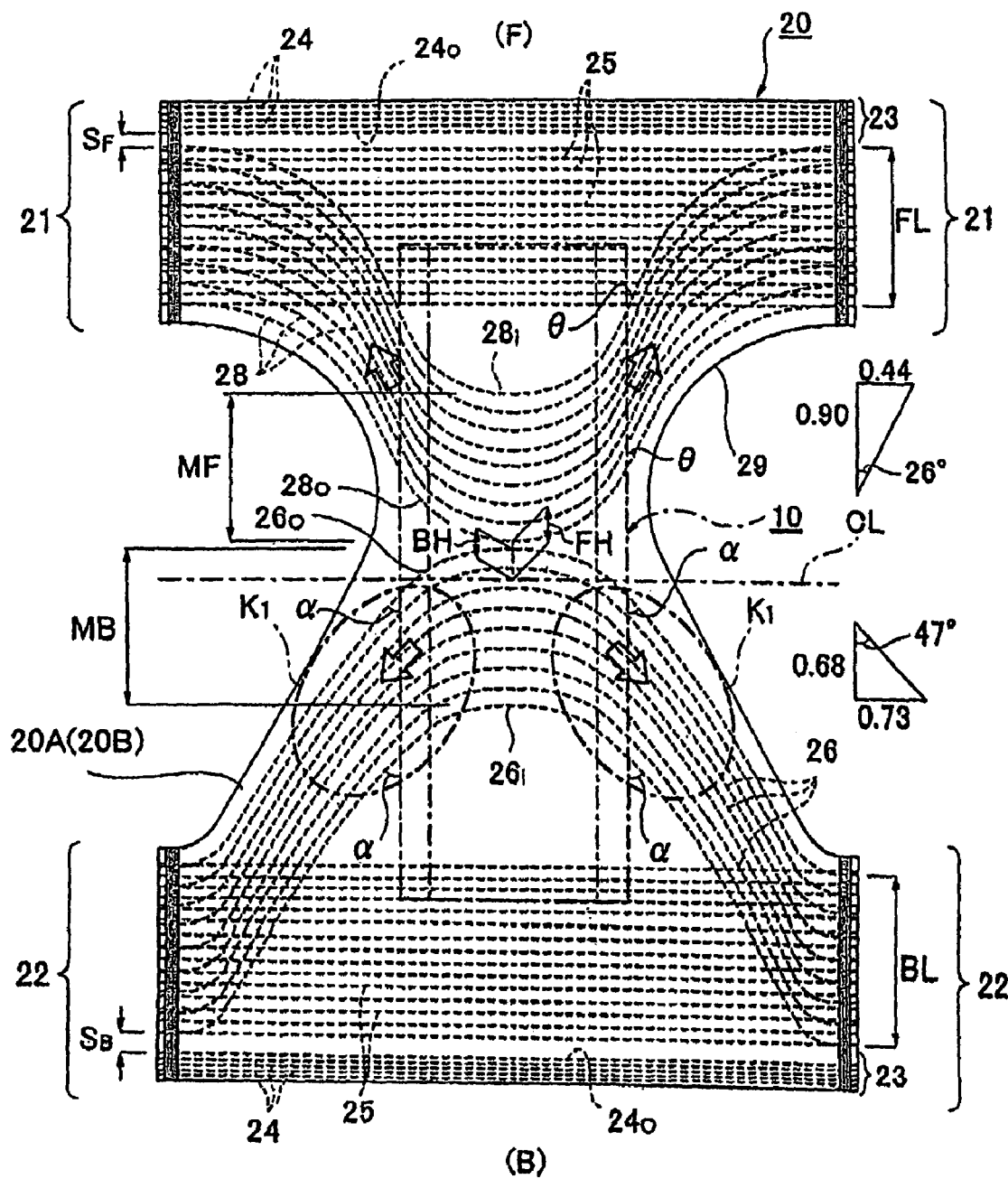
FIG. 3 is a developed view of an armoring sheet 20.

As shown in FIGS. 2 and 3, a nonwoven fabric sheet with a two-layered structure comprising a upper nonwoven fabric 20A and a lower layer nonwoven fabric 20B is used as armoring sheet 20, and various elastic members are arranged between the upper nonwoven fabric 20A and the lower layer nonwoven fabric 20B for exhibition of elasticity. As a plane shape, the armoring sheet 20 has a shape similar to a sandglass as a whole by depressed cut lines around legs 29 formed in order to give leg openings in the middle part of both side, respectively.

Especially, in the shape of a developed form shown in FIG. 3, the armoring sheet 20 with the illustrated shape has, as the elastic member, waist portion elastic members 24, 24, . . . , arranged around the waist opening 23; a plurality of hip surrounding elastic member groups 25, 25, . . . , arranged at the front F and the back B in the horizontal direction while being vertically spaced; and a plurality of curved elastic member groups 26, ..., 28, ... extending, at each of the front F and the back B, from side portion jointing edge for jointing the front F and the back B in one side, to the crotch side, reaching the side portion jointing edge for jointing the front and the back in the other side, while bypassing the crotch side, and arranged at a spacing without intersecting with each other. The armoring sheet 20 does not have what is called "leg surrounding elastic member" that substantially continuously extends along with the leg surrounding cut lines 29.

Hereinafter, detailed descriptions will be given for every various elastic members.

The waist portion elastic members 24, 24, ... are a plurality of rubber thread-like members arranged with a spacing in a vertical direction in the vicinity of the waist opening edge within the area of side portion jointing edges 21 and 22 where the front F and the back B are joined together. The elastic members 24, 24, ..., have a function for wearing of the paper diaper to a human body by applying an elastic force for tightening of the circumference of the waist portion of the human body. Rubber threads are used for the waist portion elastic members 24 in the illustrated example, and, for example, elastic members in a tape shape may also be used.

The hip surrounding elastic member groups 25, 25, ... are rubber thread-like elastic members that are horizontally arranged with a spacing almost over the area of upper portion to the lower portion in a vertical direction within the side portion jointing edges 21 and 22. The hip surrounding elastic member groups 25, 25, ..., have a function for forcing the paper diaper to the human body by applying a horizontal elastic force to the respective waist portions of the front F and the back B. The border between the waist portion elastic members 24, 24, ..., and the hip surrounding elastic member groups 25, 25, ..., may not be necessarily clearly defined. For example, some of the elastic members in a side of the upper portion out of the elastic members vertically arranged with a spacing in a horizontal direction in the front F and the back B may function as an elastic member of the waist portion even though the number may not be specified, and the remaining elastic members should just function as the waist portion elastic members.

In the back B, the back side curved elastic member groups 26, 26, ..., arranged in addition to the hip surrounding elastic member groups 25, 25, ..., include a plurality of rubber thread-like elastic members, in illustrated example, nine rubber thread-like elastic members. These are arranged to extend from the side portion jointing edge 22 in one side to the crotch portion almost along with the leg surrounding cut line 29 so as to reach the side portion jointing edge 22 of the other side, bypassing the crotch portion and almost along the leg surrounding cut line 29 in the opposite side. The back side curved elastic member groups 26, 26 ... are arranged with a spacing without mutual intersection. The back side curved elastic member group 26, 26, ..., have different arrangement mode from that in conventional elastic members around legs. That is, the elastic member groups are not arranged substantially in one bundle of approximately 2 or 3 elastic members at dense spacing, but 5 or more, preferably 7 or more, of the elastic members are arranged with a predetermined spacing so as to form a predetermined elastic zone.

The back side curved elastic member groups 26, 26, ..., have their starting/trailing ends connected at a predetermined spacing substantially over the range from the upper portion to the lower portion of the side portion jointing edge for jointing the front F and the back B. They have an arrangement pattern so as to give an angle of 35° or more of an intersection angle α on the acute angle side between the back side curved elastic member groups 26, 26, ..., and the absorbent body 10 at the side edge of the absorbent body 10, preferably 40° or more, and more preferably 45° or more. Incidentally, in the illustrated example, they are arranged so that the intersection angle α may give around 47°. The intersection angle α is desirably 60° or less in view of the balance of a horizontal component of force and a vertical component of force.

In the side portion jointing edges 21 and 22 for jointing the front F and the back B, the elastic member 26$i$, positioned closest to the waist opening, of the curved elastic member groups 26, 26, ..., is spaced at a distance SB of 20 mm or less from the lowermost elastic member 24$_0$ of the waist portion elastic members 24, 24, .... As a result, when the wearer pulls up the sides of the waist portion, the front side of the paper diaper can be easily pulled upward by the elastic force of the curved elastic members 26, 26, ..., thereby to improve the wearing easiness.

Furthermore, the back side curved elastic member groups 26, 26, ... are desirably turned, inarcuate curves, at the bypassing portion in the crotch portion. In the elastic member, its elastic force usually acts in a tangential direction. However such turning in the arcuate curve in the crotch portion minimizes the force acting in a width direction of the absorbent 13, allowing avoidance of shrink of the absorbent 13 in the crotch portion.

Especially, in the illustrated paper diaper 1, in order to fit the armoring sheet 20 corresponding to the bulging shape in the back B, the elastic member groups 26, 26, are so arranged at a relatively gentle inclination angle that the elastic force may act in the direction met as much as possible in the direction along the bulge of the back. When the elastic members 26, 26, ... are arranged at α=47° of intersection angle, 73% of the applied elastic force can act as a horizontal component of force, thereby allowing the armoring sheet 20 to contact to the human body so closely on the body as to wrap the back. As a result, the absorbent body 10 is not shrunken on the central side, but is closely fitted on the human body thereby to enhance the leakage-proof effect.

Furthermore, the arrangement spacing of the back side curved elastic member groups 26, 26, ..., in the side portion jointing edges 21, 22 for jointing the front F and the back B, that is, the arrangement spacing of them, in a section BL where the elastic members are arranged in the side portion side edges 21 and 22, is made substantially the same as the arrangement spacing of the back side curved elastic member groups 26, 26, ..., in a section MB where the elastic member are arranged in the crotch portion. The elastic member 26$_0$, positioned closest to the crotch side, of the back side curved elastic member groups 26, 26, ..., is arranged so as to draw a curved line shape giving a distance BH of ±50 mm or less from the crotch portion folding line CL, and preferably 35 mm or less. The arrangement spacing of the back side curved elastic member groups 26, 26, ..., is arranged equivalently at the side portion jointing edges 21, 22 and at the crotch portion, thereby allowing avoidance of concentration of elastic force, and contact of whole of the armoring sheet 20 to the human body with equivalent balance. The lines drawn by the back side curved elastic member groups 26, 26, ..., have curved shapes of large waves bypassing the area in the vicinity of the crotch portion, so that the armoring sheet 20 can be firmly held in close contact with respect to the human body.

The back side curved elastic member groups 26, 26, ..., arranged at the back B side are desirably biased in the crotch portion to the front F side based on the crotch portion folding line CL of the diaper. The bias of the back side curved elastic member groups 26, 26, ..., in the crotch portion, to the side of the front F based on the crotch portion folding line CL of the diaper enables elimination of the slip-down of the diaper in the back side and the slack of the armoring sheet 20 to enhance of fit to the human body.

On the other hand, the abdomen side curved elastic member groups 28, 28, ..., arranged in the front of the armoring sheet 20 besides the hip surrounding elastic member groups 25, 25, ... are also a plurality of fiber elastic members, in illustrated example nine, arranged with a spacing without intersection, and the curved elastic member groups 28, 28, ..., extend from the side portion jointing edge 21 of one side to the crotch side, and reach the side portion jointing edge 21 of the other side bypassing the crotch side. The abdomen side curved elastic member groups 28, 28, ... are arranged with a spacing and without intersection. The abdomen side curved elastic member groups 28, 28, ... are different in the arrangement mode from the leg surrounding elastic members of the prior art. That is, the elastic member groups are not arranged substantially in one bundle of approximately 2 or 3 elastic members at dense spacing, but 5 or more, preferably 7 or more, of the elastic members are arranged with a predetermined spacing so as to form a predetermined elastic zone.

The abdomen portion elastic member groups 28, 28, ..., have their starting/trailing ends connected at a predetermined spacing substantially over the range from the upper portion to the lower portion of the side portion jointing edge 21, 21 for jointing the front F and back B, and in the intersection with the side line of the absorbent body 10. The abdomen portion elastic member groups 28, 28, ... are arranged with an arrangement pattern in which the acute angle side intersection angle θ with the absorbent body 10 side line gives 30° or less between the abdomen side curved elastic member groups 28, 28, ..., and the absorbent body 10 side line, and preferably 28° or less. Incidentally, in the illustrated example, they are arranged so that the intersection angle θ may give about 26°. The intersection angle θ is desirably 20° or more in view of the balance of a horizontal component of force and a vertical component of force.

In order to minimize the force of acting in a crosswise direction of the absorbent 13 and to avoid shrink of the absorbent 13 in the crotch portion, the abdomen side curved elastic member groups 28, 28, ... are desirably turned in arcuate curves at the bypassing part of the crotch portion.

It is found that since the paper diaper 1 of the embodiment does not have a bulging portion in the back of the human body unlike the bulging as in front side portion of the human body, the slip-down of the paper diaper has a prominent tendency to occur mainly on the front side F. Based on the finding, the elastic member groups 28, 28, ... are arranged with relatively sharp angle of inclination. As in the illustrated example, disposition of the elastic members 28, 28, ..., at θ=26° of the intersection angle can make the 90% of the elastic force applied thereto act as a component of force in an upward direction, allowing effective prevention of slipping down of the paper diaper.

In the side portion jointing edges 21, 22 for jointing the front F and the back B, the elastic member 28i, positioned closest to the waist opening, of the abdomen side curved elastic member groups 28, 28, ..., is arranged so as to give a 20 mm or less of the distance SF from the lowest side elastic member $24_0$ of the waist portion elastic member. When the wearer pulls up the sides of the waist portion, the front side of the paper diaper can be easily pulled upward by the elastic force of the abdomen side curved elastic member groups 28, 28, ..., thereby to improve the wearing easiness.

Furthermore, the arrangement spacing of the abdomen side curved elastic member groups 28, 28, ..., in the side portion jointing edges 21 and 22 for jointing the front F and the back B, namely, the arrangement spacing in the elastic member arranged section FL of the side edges 21 and 22 is made substantially the same as the arrangement spacing of the abdomen side curved elastic member group 28, 28, ..., in the elastic member arranged section MF of the crotch portion. The elastic member $28_0$, positioned closest to the crotch side, of the abdomen side curved elastic member groups 28, 28, ..., is arranged so as to draw a curved line shape giving a distance FH of ±50 mm or less from the crotch portion folding line CL, and preferably 35 mm or less. The arrangement spacing of the abdomen side curved elastic member groups 28, 28, ..., arranged equivalently at the side jointing edges 21, 22 and at the crotch portion allows avoidance of concentration of elastic force, and contact of whole of the armoring sheet 20 to the human body with equivalent balance. The lines drawn by the back side curved elastic member groups 28, 28, ..., have the curved shapes of large waves bypassing the area near the crotch portion, so that the armoring sheet 20 can be firmly held in close contact with respect to the body.

Here, although a part of the abdomen side curved elastic member groups 26, 26, ..., may have intersections with a part of the back side curved elastic member groups 28, 28, ..., in the crotch portion, the elastic member $28_0$ positioned closest to the crotch side of the abdomen side curved elastic member groups 28, 28, ..., and the elastic member $26_0$ positioned closest to the crotch side of the back side curved elastic member groups 26, 26, ..., which have been arranged in the back side B are preferably closely arranged in the crotch portion without mutual intersection. The distance between them (FH-BH) is preferably 10 to 20 mm. In the case of the latter, the forced contact to the human body side of the absorbent body 10 with the equivalent pressure of the curved elastic member groups 28, ..., and 26, ..., in the crotch portion blocks clearance with the human body, leading to demonstration of high leakage preventive effect.

Figure 4:
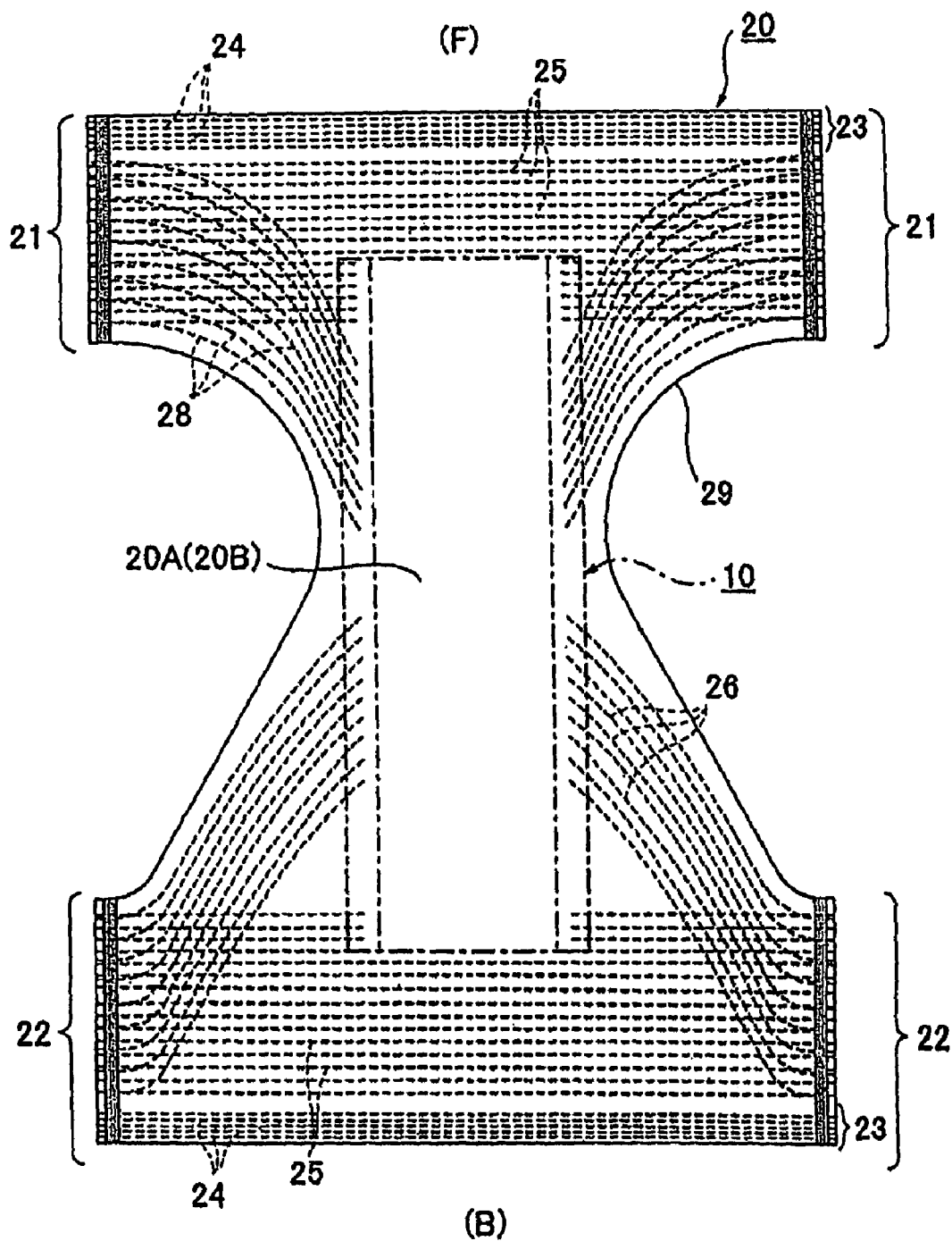
FIG. 4 is a developed view of a modification of the armoring sheet 20.

Furthermore, in the above-described example, the hip surrounding elastic member groups 25, 25, ..., and the curved elastic members 26, ..., and 28, ..., that have been arranged in the front F and the back B are continuously arranged on the absorbent body 10, and the elastic members that cross over the absorbent body 10 may be cut as shown FIG. 4 to give discontinuity. The discontinuity of the elastic members on the absorbent body exhibits higher preventive effect of shrink of the absorbent 13. Here, irrespective of whether the elastic members have discontinuity on the absorbent body 10 or not, the above-described effect is exhibited as long as the hip surrounding elastic member group 25, 25, ..., and the curved elastic members 26, ..., and 28, ... are arranged as mentioned above in the condition before cutting.

Figure 7:
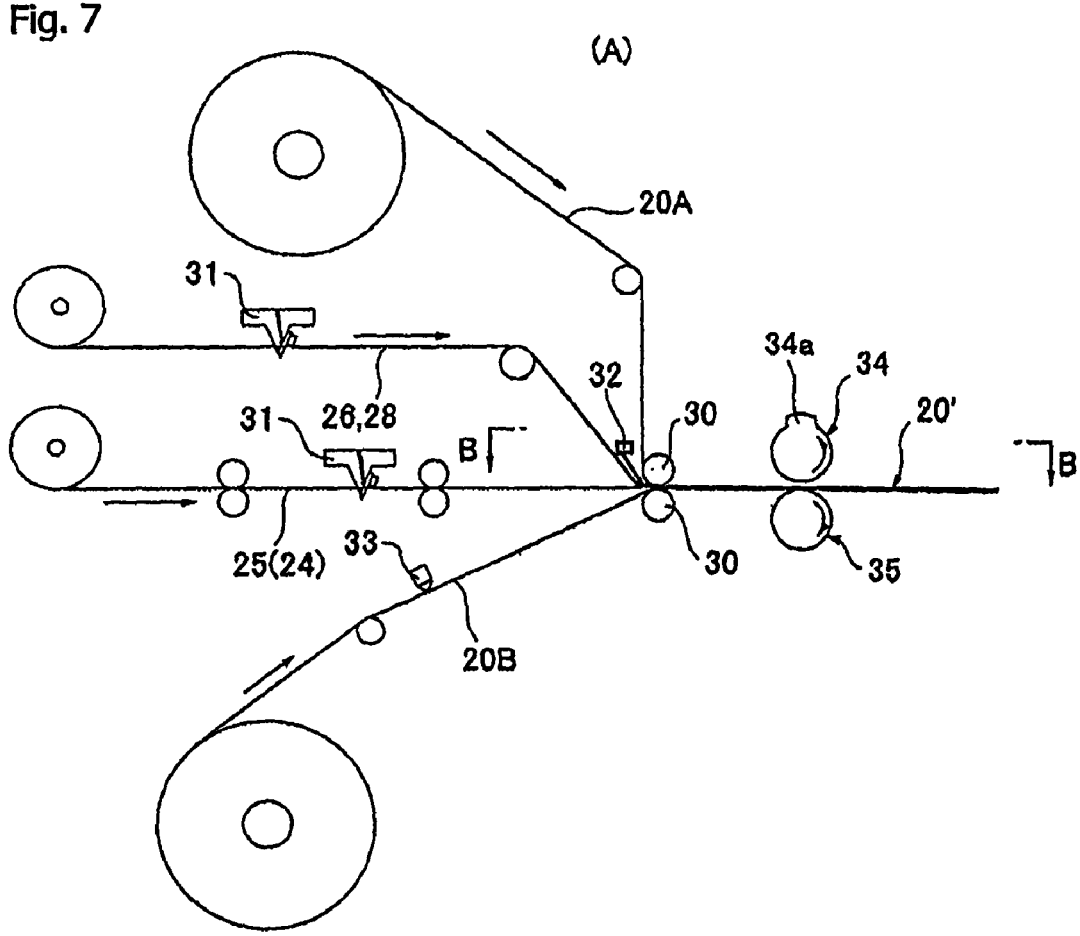
FIG. 7 is an assembly outline of the armoring sheet 20, where
Figure 7:
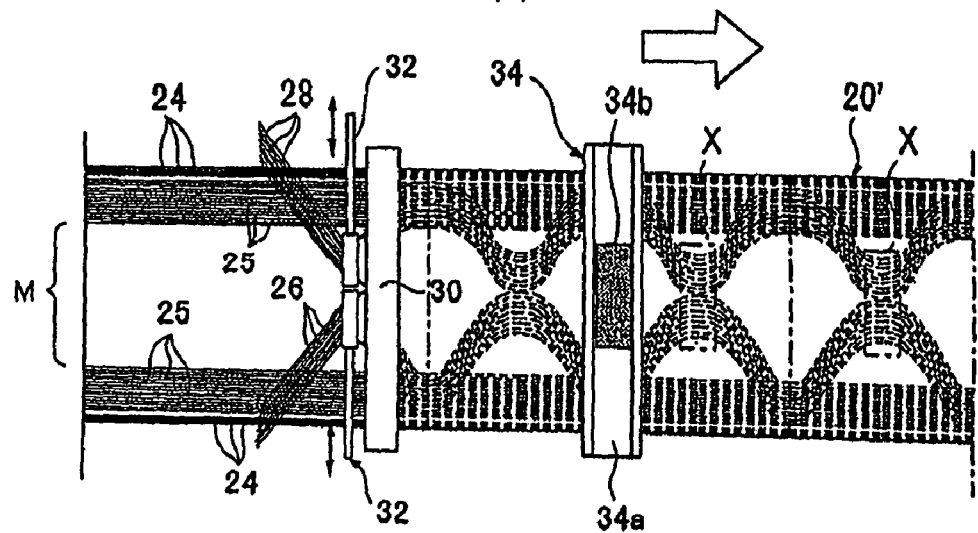

On the other hand, the above-described armoring sheet 20 can be produced, for example, as follows. That is, as shown in FIG. 7, the upper nonwoven fabric 20A is supplied on the upper part of the feed roller part 30, and the lower layer nonwoven fabric 20B is supplied to the lower part. Various elastic members (the waist portion elastic members 24, the hip surrounding elastic members 25, the back side curvature elastic members 26, and the abdomen portion elastic members 28) are supplied between the upper nonwoven fabric 20A and the lower nonwoven fabric 20B, whereby the armoring sheet 20 is continuously assembled.

The waist portion elastic members 24, 24, ..., and the hip surrounding elastic member 25, 25, ... are introduced linearly along the direction of the conveying line into the feed roller part 30. On the other hand, the curved elastic members 26, ..., and 28, ... are introduced into the feed roller part 30, while they are curved and snaked by the guides 32. As FIGS. 8 to 15 show, each guide 32 has, at its fore end portion, guide paths 32X, 32X, . . . , for the elastic members 26, . . . , and 28, . . . , so as to guide them in a predetermined curved shape by its oscillation (reciprocation) caused by a not illustrated driving mechanism such as a cylinder at a predetermined speed in a cross direction (a direction perpendicular to the machine direction of the conveying line, and in this case, a width direction of the continuous webs (sheets 20A and 20B)). Furthermore, the plurality of guide paths 32X, 32X, . . . are arranged parallel, at a predetermined spacing along the cross direction, and each curved elastic member 26, . . . 28, . . . , is guided through each guide path 32X, 32X, . . . . Therefore, all the curved elastic members 26 and 28 are arranged with equivalent arrangement spacing in their whole area, that is, in both of the crotch portions and the side portion jointing edges 21 and 22.

Figure 9:
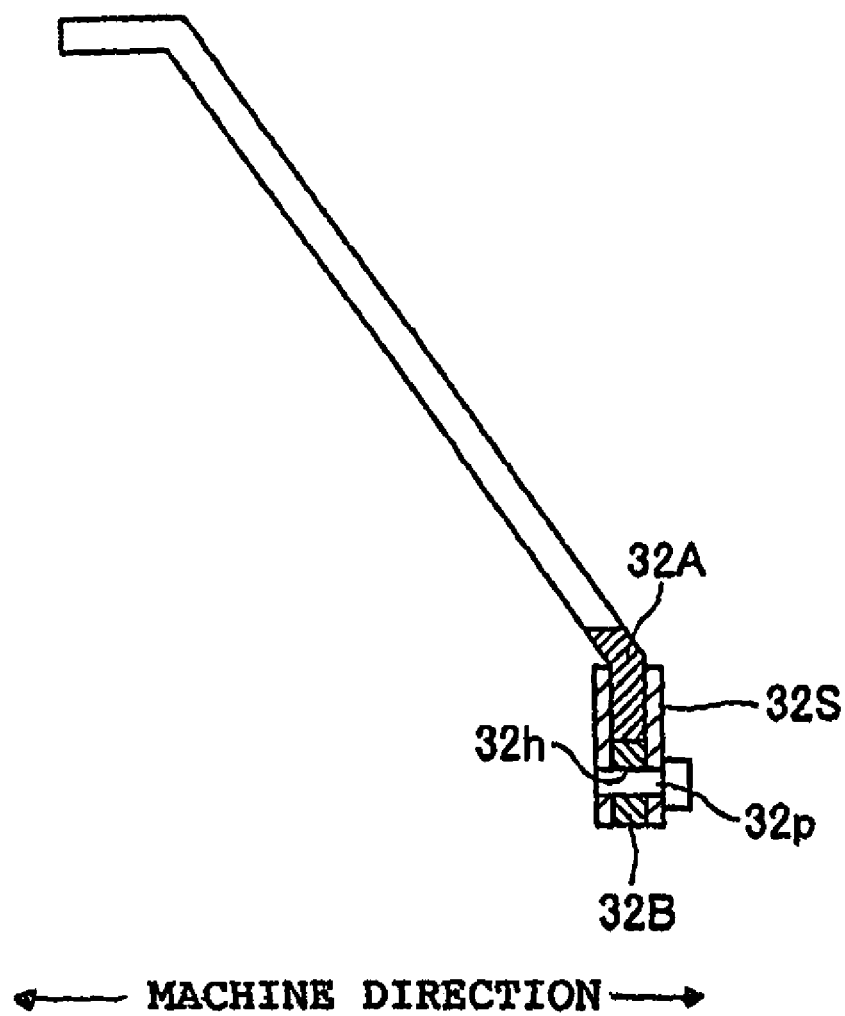
FIG. 9 is a IX-IX sectional view of FIG. 8.
Figure 10:
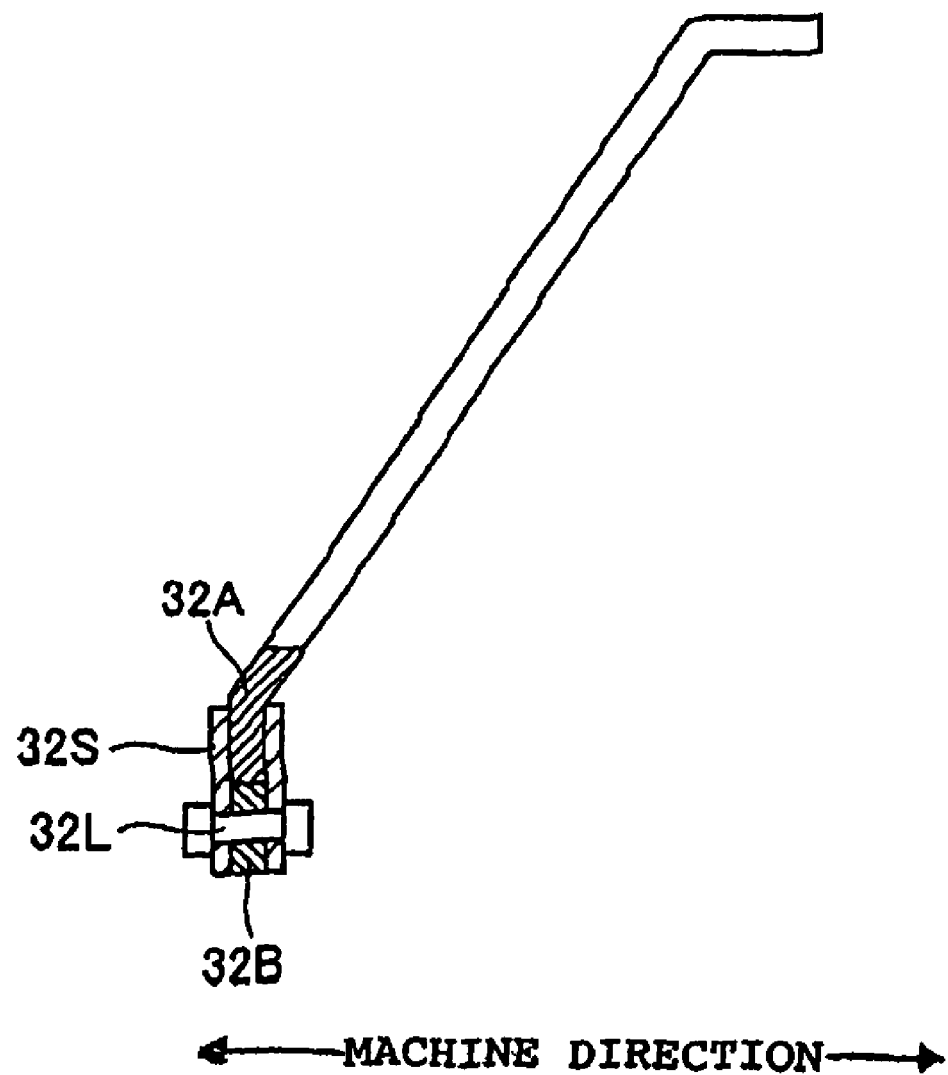
FIG. 10 is a X-X sectional view of FIG. 8.

In more detail, the end portion of the guide 32 includes an upper part 32A attached to the not illustrated driving mechanism such as a cylinder, and a lower part 32B detachably attached to the upper part 32A. As shown in FIGS. 9 and 10, the supporters 32S, 32S projecting in the lower part 32B side are provided in both ends in the cross direction of the upper part 32A, respectively. One end part of the lower part 32B is freely rotatably linked through a link shaft 32L with respect to one of the supporter 32S, and the other end of the lower part 32B is removably fixed to the other supporter 32S. As shown in FIG. 9, such fixing mechanism includes a pin insertion hole 32h formed so as to pass through at least from the above other supporter 32S to the inside of the above other end of the lower part 32B, and a lock-pin 32p removably inserted in the pin insertion hole 32h, in a condition that the guide path 32X is formed with the lower part 32B and the upper part 32A. The lower part 32B is fixed to a mounting position by allowing the lock-pins 32p to pass through the supporter 32S so as to be inserted into the above other end of the lower part 32B. On the other hand, in order to unfix the lower part 32B from the upper part 32A, the lock-pin 32p is removed, and then the lower part 32B is pivoted around the link shaft 32L as shown in FIG. 12, while the link is maintained between the lower part 32B and the upper part 32A.

For substitution of such a link structure, a simpler structure may also be employed in which the upper part 32A and the lower part 32B are fixed removably with screws.

Figure 8:
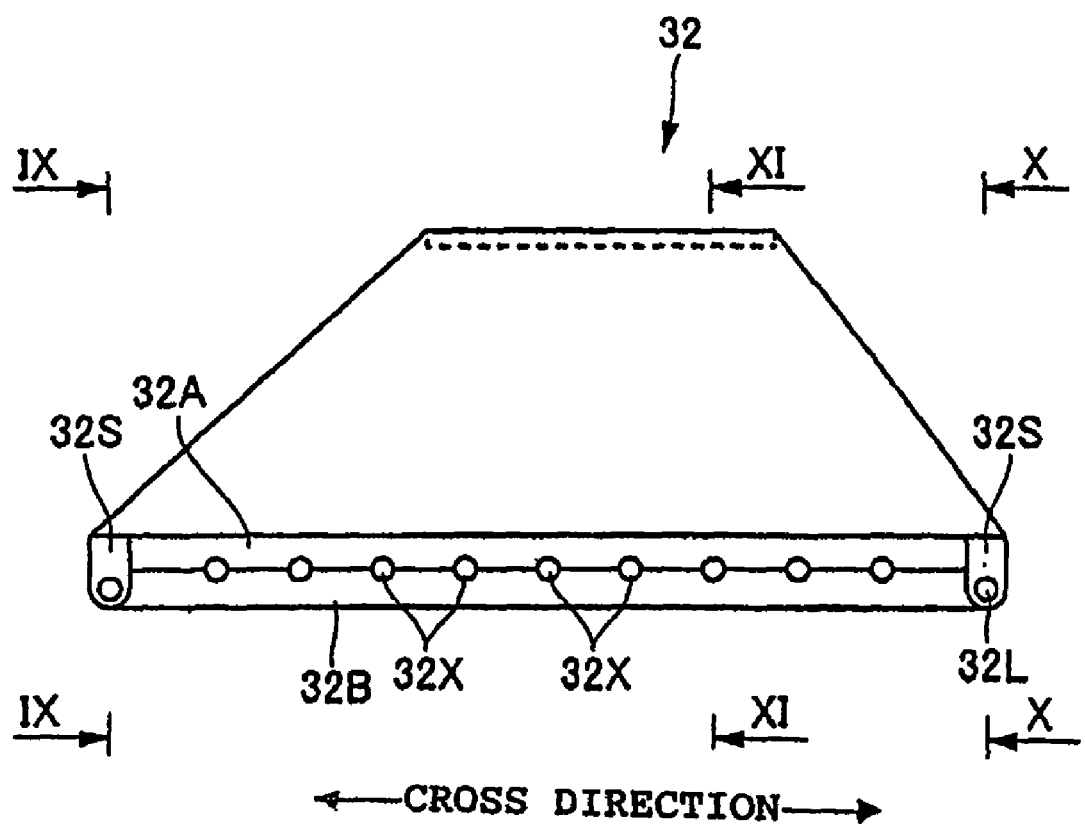
FIG. 8 is a front view of a guide.
Figure 12:
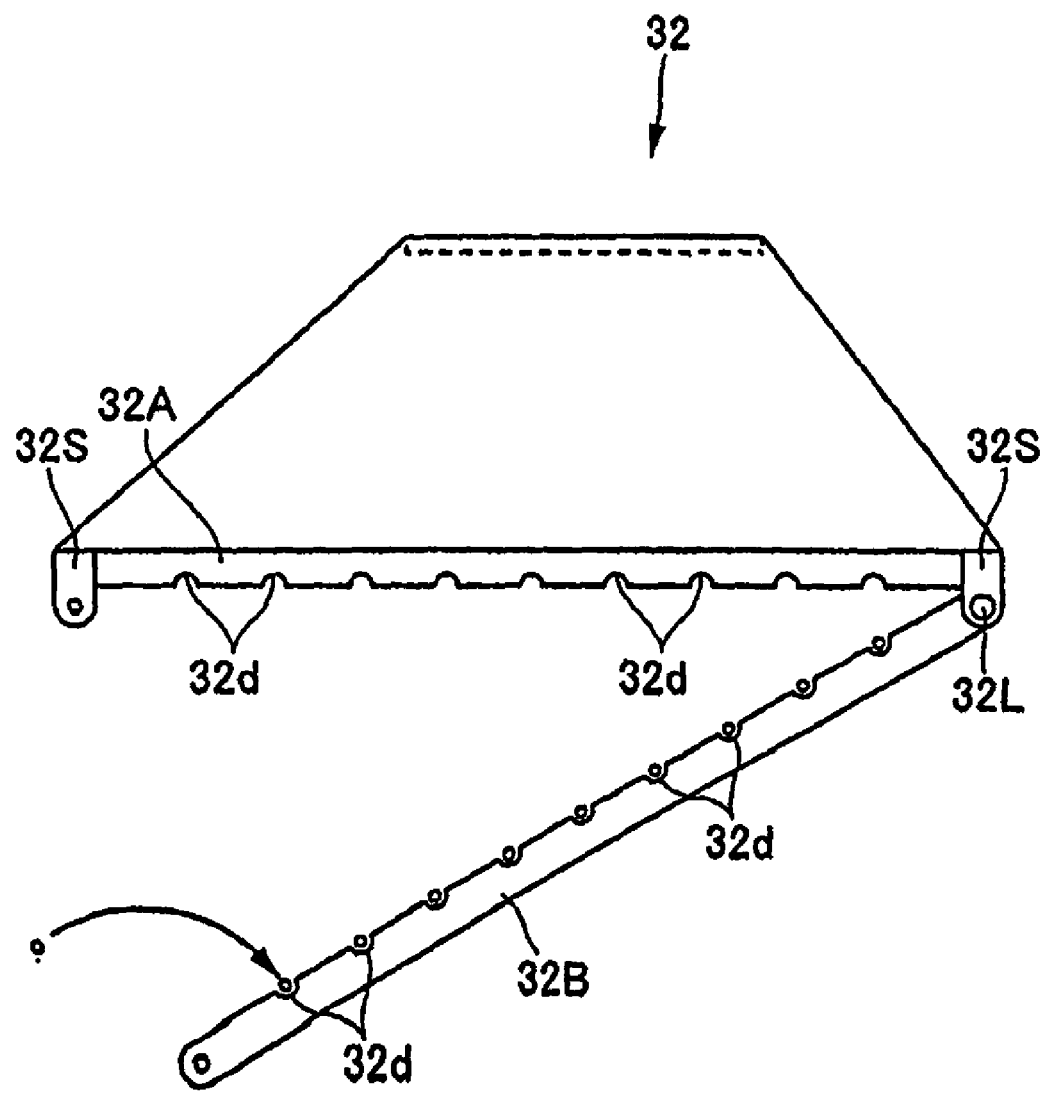
FIG. 12 is a front view of the guide.

As shown in FIG. 12, each opposed face of the upper part 32A and the lower part 32B has a plurality of (in the illustrated example, nine) grooves 32d, 32d, . . . , passing through from one side to the other side currently, formed in parallel along with the machine direction (direction of the conveying line) with a predetermined spacing in the cross direction. The grooves 32d, 32d, . . . , of the upper part 32A, and the grooves 32d, 32d, . . . , of the lower part 32B are provided in the cross direction so as to be corresponding each other. As shown in FIG. 8, while the lower part 32B is attached to the upper part 32A, their corresponding grooves 32d, 32d, . . . are coupled together to form the guide paths having closed circumferences, respectively. Of course, there may be another configuration that only either one of the upper part 32A and the lower part 32B, for example, only the upper part 32A may have the grooves and thus the lower part 32B functions as a mere lid.

Figure 11:
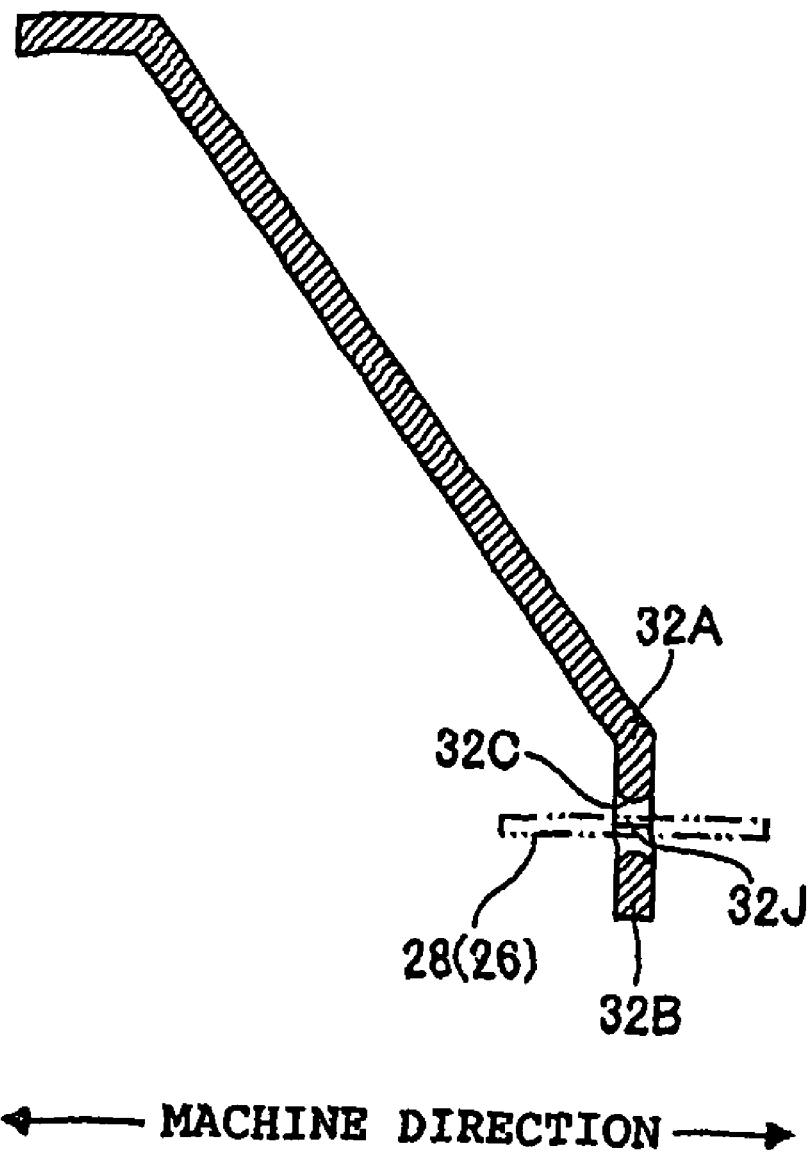
FIG. 11 is a XI-XI sectional view of FIG. 8.

The guide path 32X preferably has a smaller friction with the elastic members 26, 28. In detail, as shown in FIG. 11, the guide path 32X can be formed so that it may have a smooth curved shape 32C from the edge of the entrance to the edge of the exit with a bulge at its intermediate part. Adding to or aside from such shaping, the interior surface of the guide path 32X may also have a surface treatment such as a fluorine treatment, Kanuc treatment, etc. for reduction of friction.

Figure 13:
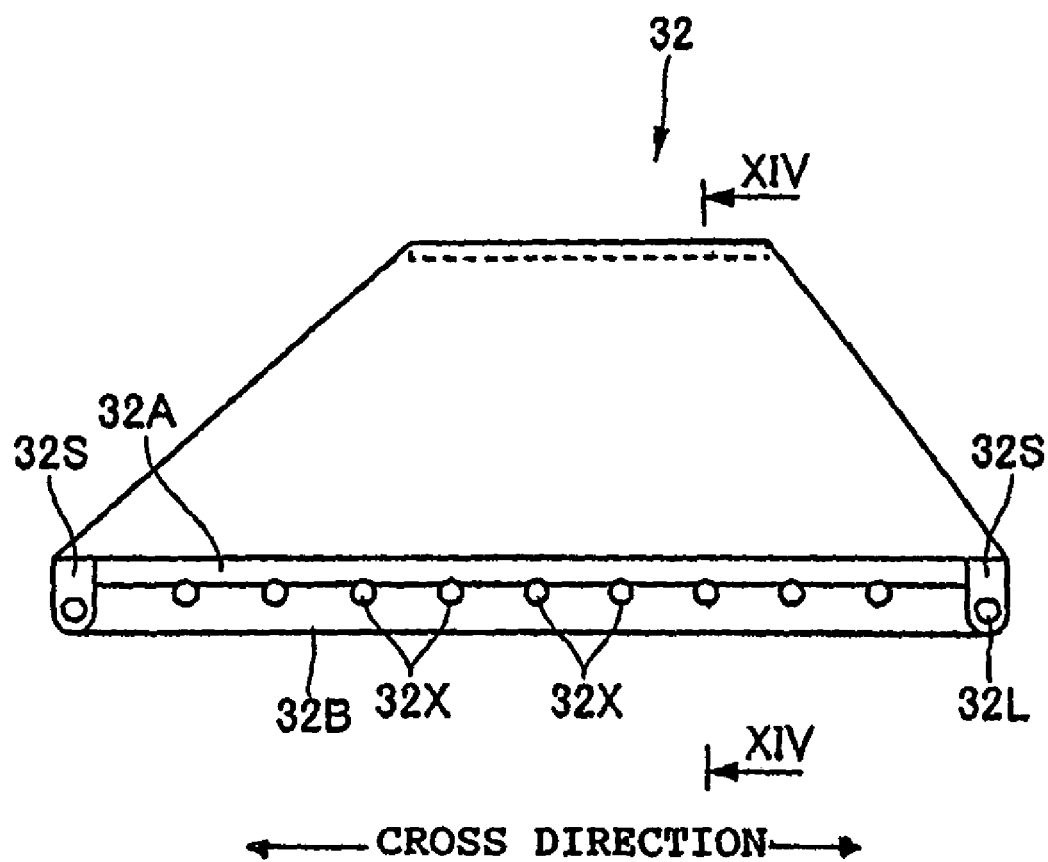
FIG. 13 is a front view of another guide.
Figure 14:
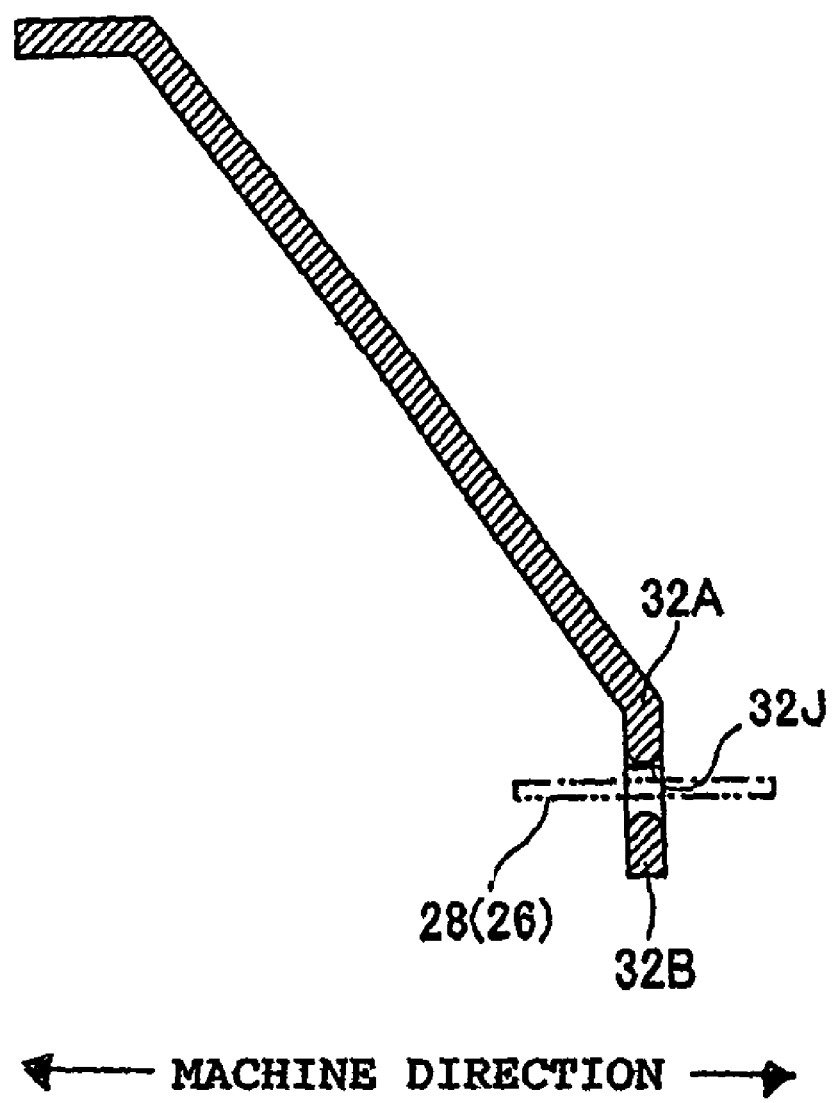
FIG. 14 is a XIV-XIV sectional view of FIG. 13.
Figure 15:
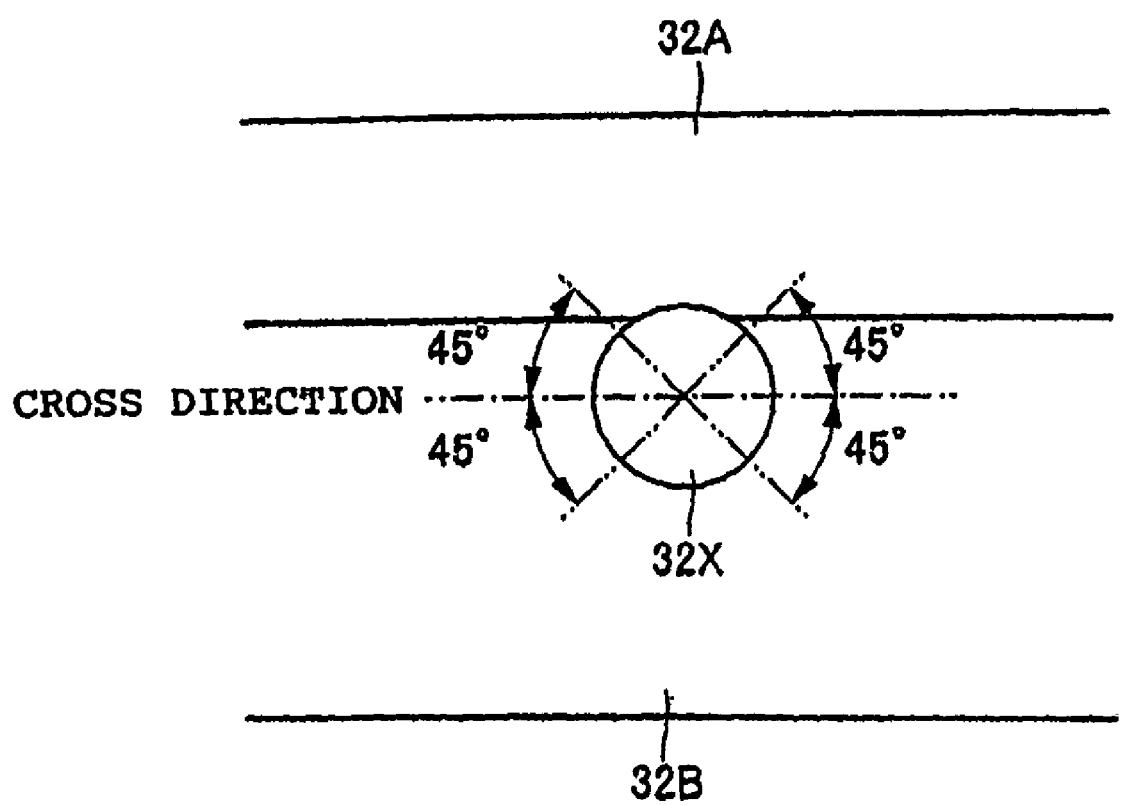
FIG. 15 is a principal part expanded front view of the guide.
Figure 16:
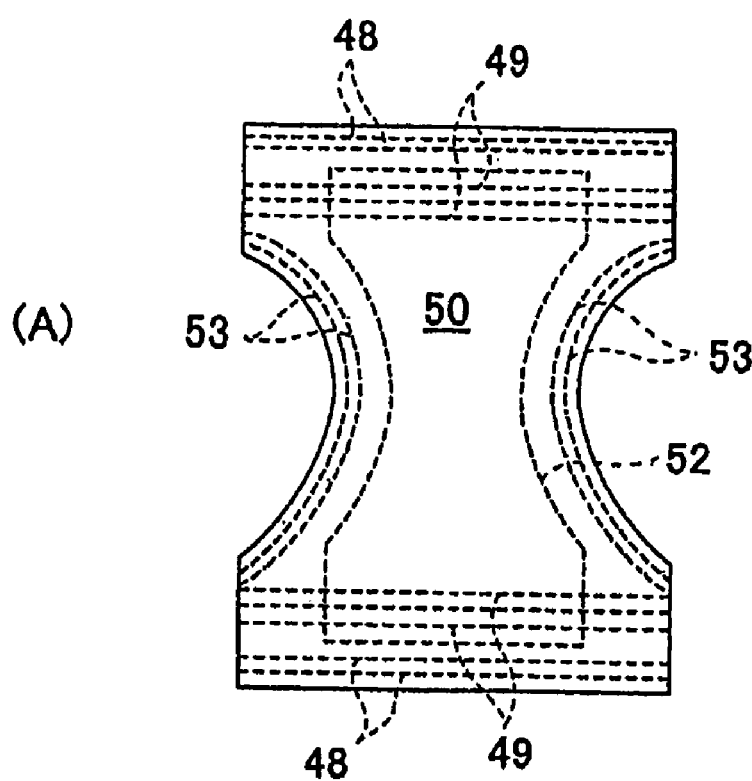
FIG. 16 shows a conventional pants-type disposable paper diaper (No. 1), where
Figure 16:
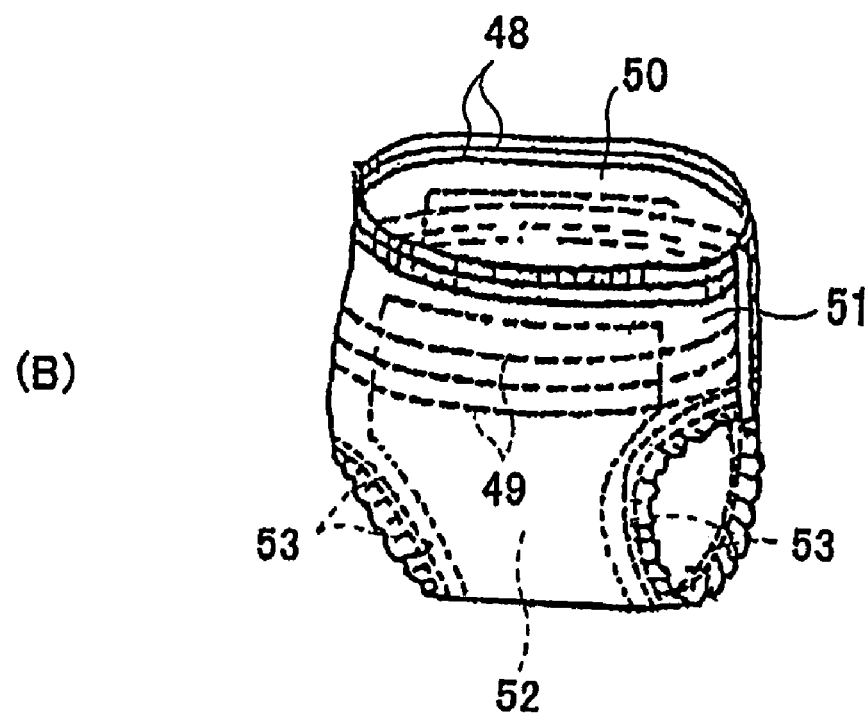
Figure 17:
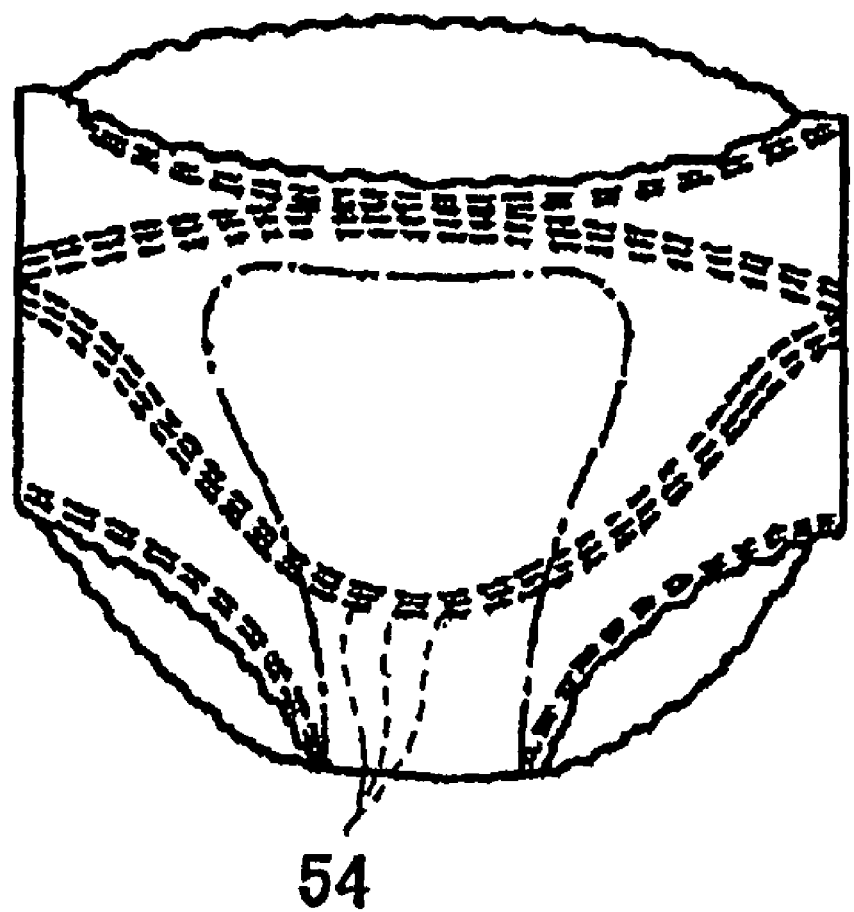
FIG. 17 is a front view showing a conventional pants-type disposable paper diaper (No. 2)
Figure 18:
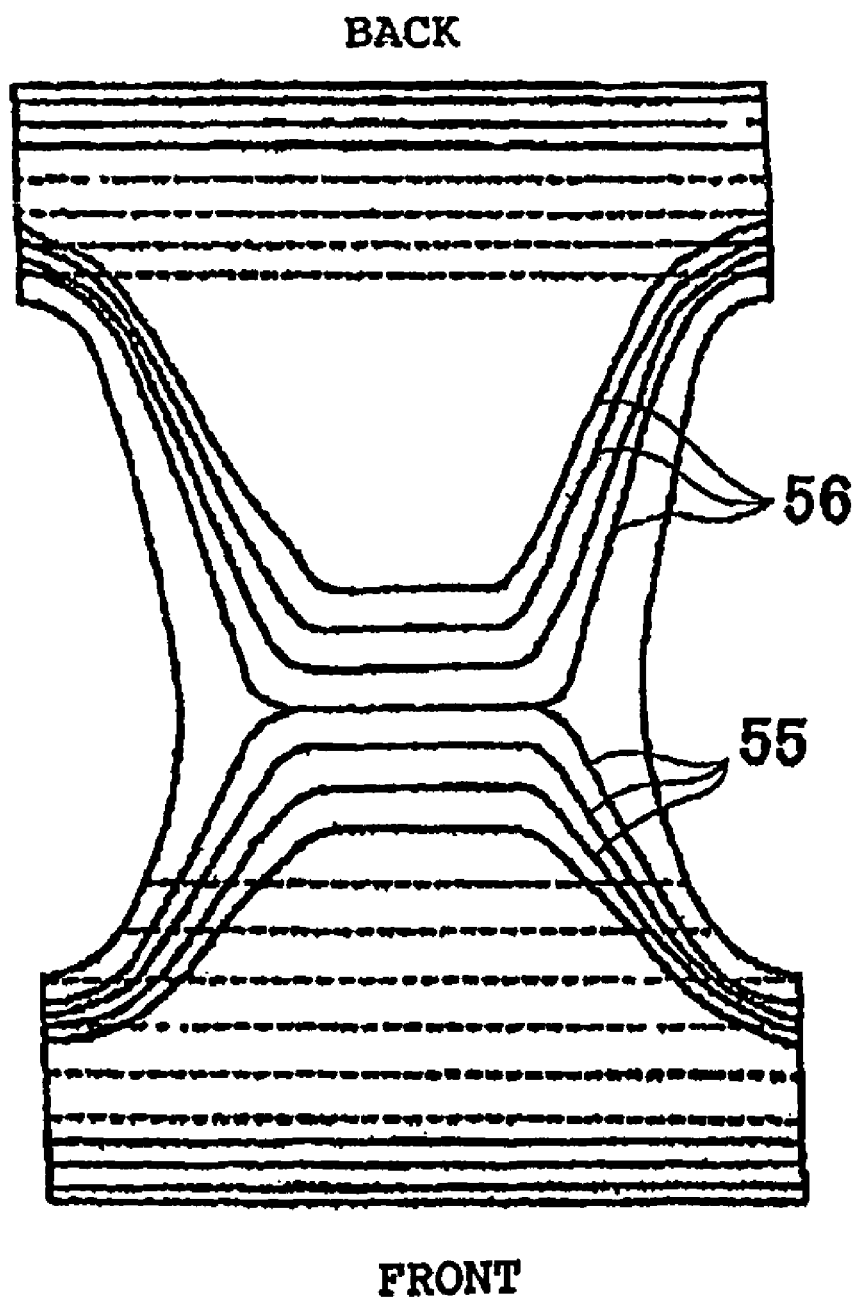
FIG. 18 is a developed view showing a conventional pants-type disposable paper diaper (No. 3)
Figure 19:
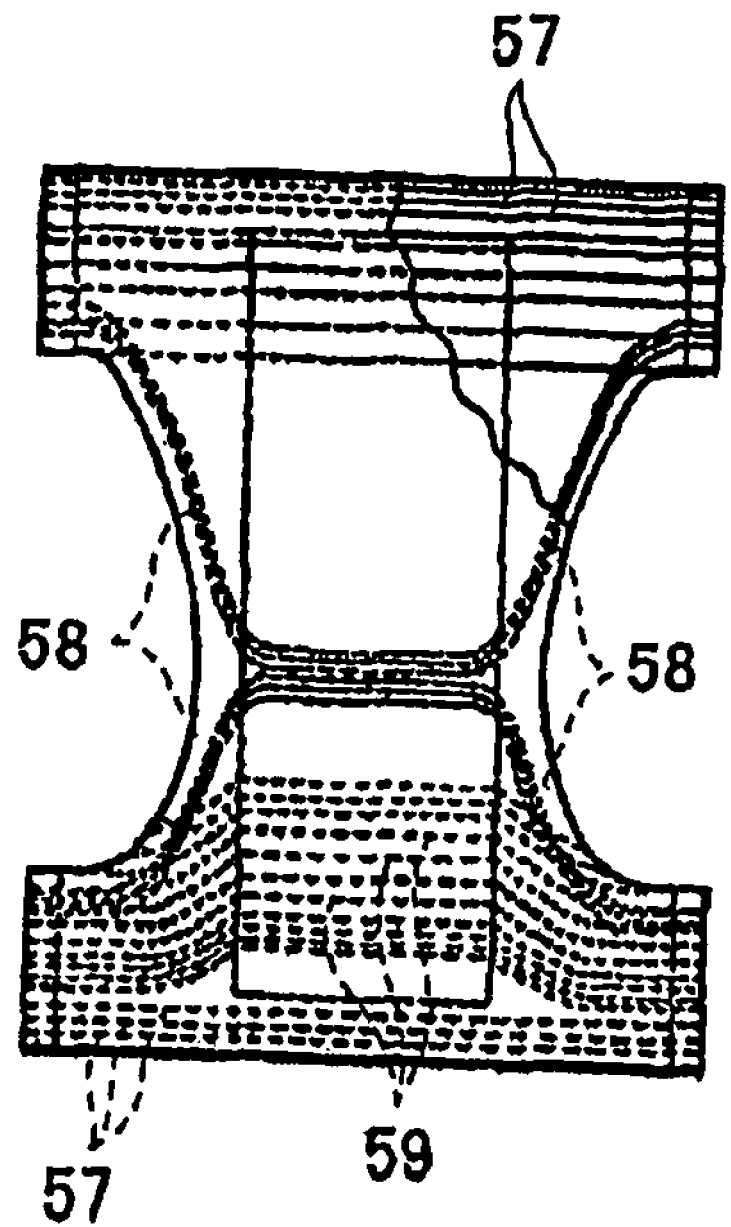
FIG. 19 is a developed view showing a conventional pants-type disposable paper diaper (No. 4)
Figure 20:
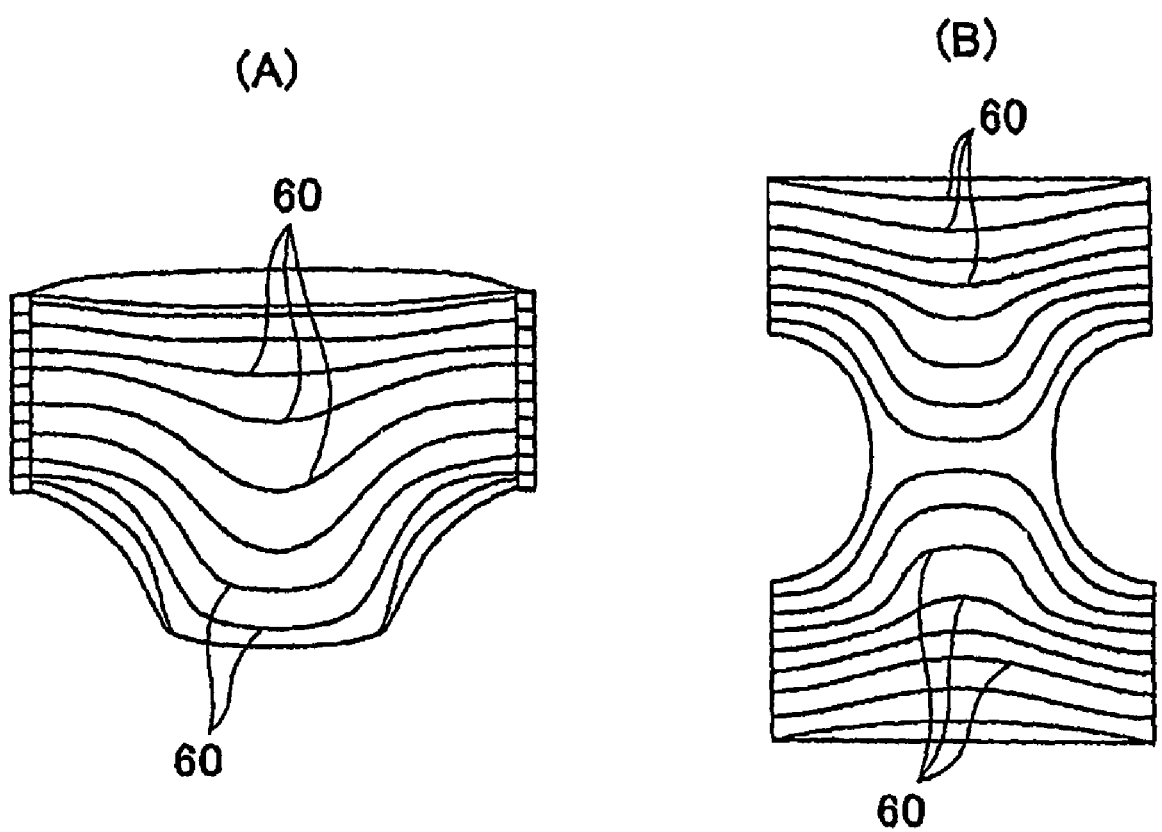
FIG. 20 shows a conventional pants-type disposable paper diaper (No. 5), where

When the elastic members 26, 28 contact, due to the oscillation of the guide 32, a joint 32J of the upper part 32A and the lower part 32B exposed to the interior surface of the guide path 32X, there may occur possible yarn breakage of the elastic members 26, 28 by friction. Accordingly, in the present invention as shown in FIGS. 13 and 14, the joint 32J is formed so that it may not be located in both sides in the cross direction. The both sides in the cross direction with respect to the guide path 32X can be defined suitably. For example, as shown in FIG. 15, the both sides have the angle ranges, around the center of each guide path, to be ±45 degrees with respect to the cross direction in the case where the guide path 32X is a circular hole extending along the machine direction. In examples shown in FIGS. 13 to 15, in order to avoid the positioning of the joint 32J within the range in the both sides, the groove of the upper part 32A is formed shallower, while the groove of the lower part 32B is formed deeper.

Using the guide 32 having such a configuration, when the elastic members 26, 28 are newly needed to be inserted through the guide 32 in case of yarn breakage of the prior elastic members 26, 28, the lower part 32B is removed as shown in FIG. 12. Then, overall length of the passage is placed in an open condition in a part of the peripheral surface of the guide path 32X, whereby the elastic members 26, 28 can be inserted sideways from this open part.

In this embodiment, on the other hand, adhesion of the waist portion elastic members 24, and of the hip surrounding elastic members 25 to the sheet is achieved by applying a hot melt adhesive with a peripheral surface application device 31 onto the peripheral surface of the elastic members 24, 24, and 25, 25, and by feeding to the roller part 30.

In an intermediate zone M between the hip surrounding elastic members 25, 25, . . . of the front and hip surrounding elastic members, 25, 25, . . . of the back, the hot melt adhesive is applied with a bead application method by a coater 33, to at least one of the upper nonwoven fabric 20A and the lower nonwoven fabric 20B, in the illustrated example, to the lower nonwoven fabric 20B, so as to make a plurality of rows in a horizontal direction in the drawing with a spacing in an vertical direction in the drawing. In the intermediate zone M, the curved elastic members 26, . . . , and 28, . . . are fixed with the hot melt adhesive applied to the lower nonwoven fabric 20B.

In order to cut the curved elastic members 26, . . . , and 28, . . . , so as to be discontinuous on the absorbent body 10, the cutting processes described in JP-A-2002-35029, JP-A-2002-178428, and JP-A-2002-273808 are suitably adopted. In the cutting process for the elastic members described in these publications, briefly as shown in FIG. 7, after producing a laminated sheet 20', which is to be an armoring sheet 20, the laminated sheet 20' is inserted between an embossing heat roll 34 having a plurality of projections arranged on the surface, and a counter roll 35 facing the embossing heat roll 34. Thereby, the curved elastic members 26, . . . , 28, . . . , of the laminated sheet 20' are cut by at least one method of a pressurizing method and heating method between the projection of the embossing heat roll 34, and the counter roll 35. An area X in FIG. 7(B) shows the cutting region.

The invention claimed is:
1. A device for mounting an elastic member in an absorptive article, comprising:
a conveying line for continuously conveying a raw material to be mounted;
a feeding device for continuously feeding the elastic member; and a guide for guiding the elastic member fed from the feeding device to a mounting position on the raw material to be mounted on the conveying line, wherein:

the guide is configured to reciprocate in a cross direction perpendicular to a conveying direction of said conveying line to apply the elastic material;

the guide has a first part and a second part detachably attached to the first part, a guide path having a closed circumference is formed between the first part and the second part so that the elastic member can be guided to the mounting position through the guide path;

a joint of the first part and the second part exposed to an interior surface of the guide path is not located in both sides of the interior surface of the guide path in the cross direction;

the guide path is a circular hole extending along a machine direction, and an entire joint of the first part and the second part exposed to an interior surface of the guide path is not located within angle ranges of ±45 degrees with respect to the cross direction of angle ranges around a center of the guide path.

2. The device for mounting an elastic member in an absorptive article according to claim 1, wherein a groove passing through from one peripheral edge to another peripheral edge is formed, in a face of the first part opposed to the second part and in a face of the second part opposed to the first part, and these grooves are coupled together to form the guide path.

3. The device for mounting an elastic member in an absorptive article according to claim 1 or 2, wherein the guide is configured to have a plurality of the guide paths to be juxtaposed in a cross direction.

4. The device for mounting an elastic member in an absorptive article according to claim 1 or 2, wherein, said guide reciprocates so as to bypass mounting said elastic member on a crotch portion of said absorptive article.

5. The device for mounting an elastic member in an absorptive article according to claim 1 or 2, wherein, said guide reciprocates so that no leg surrounding elastic members are provided on said absorptive article.

6. The device for mounting an elastic member in an absorptive article according to claim 1 or 2, wherein, said absorptive article has waist band portions extending along two opposing sides and said conveying direction is parallel to said waist band portions.

* * * * *